United States Patent [19]

Simmen et al.

[11] Patent Number: 5,336,086
[45] Date of Patent: Aug. 9, 1994

[54] DENTAL IMPRESSION TRAY

[75] Inventors: Christian Simmen, Mahwah, N.J.; Nathaniel H. Lenchner, Lake Success, N.Y.

[73] Assignee: Coltene/Whaledent, Inc., Mahwah, N.J.

[21] Appl. No.: 147,981

[22] Filed: Nov. 5, 1993

[51] Int. Cl.⁵ .............................................. A61C 9/00
[52] U.S. Cl. ........................................................ 433/37
[58] Field of Search .................... 433/37, 38, 41, 42, 433/43, 44, 45, 46, 47, 48, 71

[56] References Cited

U.S. PATENT DOCUMENTS

| | | | |
|---|---|---|---|
| 3,247,844 | 4/1966 | Berghash | 433/37 |
| 3,473,225 | 10/1969 | Deuschle et al. | 433/48 |
| 3,654,703 | 4/1972 | McAdoo | 433/48 |
| 3,736,663 | 6/1973 | White | 433/38 |
| 3,878,610 | 4/1975 | Coscina | 433/37 |
| 4,146,963 | 4/1979 | Schreinemakers | 433/37 |
| 4,375,965 | 3/1983 | Weissman | 433/37 |
| 4,382,785 | 5/1983 | Lococo | 433/37 |
| 4,472,140 | 9/1984 | Lustig | 433/71 |
| 4,530,662 | 7/1985 | Andersson | 433/37 |
| 4,569,342 | 2/1986 | von Nostitiz | 433/48 |
| 4,619,610 | 10/1986 | Pelerin | 433/41 |
| 4,652,237 | 3/1987 | Cills | 433/37 |
| 4,668,188 | 5/1987 | Wolfenson | 433/37 |
| 4,689,010 | 8/1987 | Wolfe | 433/38 |
| 4,907,966 | 3/1990 | Kesling | 433/37 |
| 5,026,278 | 6/1991 | Oxman | 433/41 |
| 5,040,976 | 8/1991 | Ubel | 433/41 |
| 5,108,286 | 4/1992 | Freedman | 433/37 |

Primary Examiner—Cary E. O'Connor
Attorney, Agent, or Firm—Helfgott & Karas

[57] ABSTRACT

An impression tray for making impressions of the upper and lower teeth, the impression tray includes a mouthpiece and a handle. Sectional and quadrant impressions may also be made using this impression tray. The mouthpiece including an outer wall, inner wall and a base connected between the outer and inner walls at a bottom thereof. The handle is connected to an outer side of the outer wall at a mid-section thereof. The outer and inner walls each have vertical slits spaced along their length. The vertical slits each have a shoulder within the slit providing an interlock for the impression material displaced through the slits. The base includes a number of ribs on its top, each rib extending between the outer and inner walls and in an alternating arrangement with the slits on the outer and inner walls. Between each adjacent pair of ribs are two holes extending through the base. The base is also attached, on its bottom, to a platform structure. The platform structure provides a flat surface for the impression tray and forms reservoirs around the holes extending through the base. The combination of the ribs on top of the base and the platform structure attached to the bottom of the base provide a rigid structure, thereby producing an impression with a minimal possibility of deformation.

28 Claims, 6 Drawing Sheets

DENTAL IMPRESSION TRAY

BACKGROUND OF THE INVENTION

1. Field of the Invention

This invention relates to dental impression trays and, more particularly, to a device for producing an impression of teeth in a mouth.

2. Description of the Prior Art

Impression trays for making impressions of teeth are generally well known. The impression trays are filled with dental impression material and pressed onto a section of the teeth or against the entire upper or lower teeth in the mouth. The impression material cures while in the mouth and when the material is fully cured the impression tray is removed from the mouth. The impression created is then used to form a model of the teeth during the formation of a dental restoration.

Impression trays which are presently used have a mouthpiece, of a shape conforming generally to the bite radius of teeth, with a handle extending out from a midsection thereof. Some of these trays have holes positioned throughout the walls of the mouthpiece, providing an anchoring surface for impression material, to permit the excess flow of impression material to attach thereto. Some have holes only along the sides of the mouthpiece and others have holes on both the sides and base of the mouthpiece. Other trays have no holes positioned throughout the walls of the mouthpiece but instead use adhesive to retain the impression material.

Figure 5A:
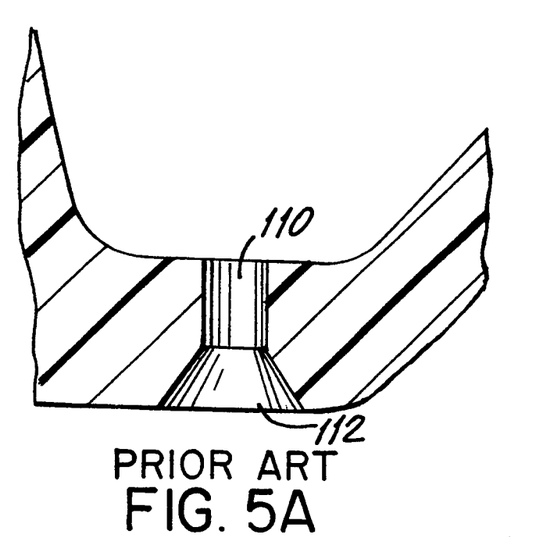
FIGS. 5a and 5b are views of a recess in the base of prior art impression trays.
Figure 5B:
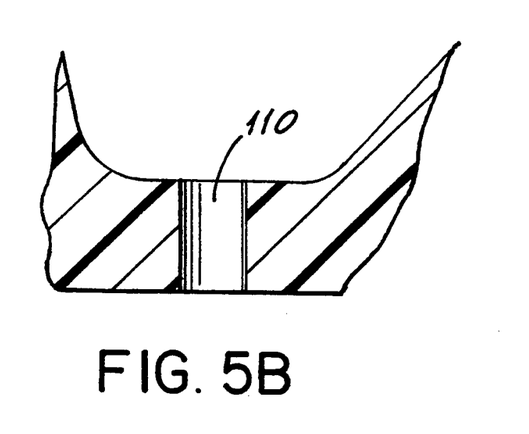

An example of a hole on the base of a mouthpiece, as is typically used in presently known impression trays, is shown in FIGS. 5a and 5b. As can be seen, the hole in FIG. 5a has the shape of an inverted funnel and the hole in FIG. 5b is cylindrical in shape. When making an impression, the impression material placed in the mouthpiece will be displaced through the small end of the hole 110 and pass through into the funnelled end of the hole 112. Further, the problem associated with these types of holes is that by seating the tray, typically two fingers are placed at the back of the tray base to guide the tray in its final position for curing of the impression material. These fingers block some holes so impressional material cannot flow through completely. In the case of FIG. 5a, there is a theoretical retaining body, i.e., the inverted funnel, in FIG. 5b there may be no retaining body at all. With the hole as shown in FIG. 5a, there is the disadvantage that when pulling the tray out of the mouth with the cured impressional material, forces occur that act on the retention ability of the funnel. Since rubber material has a high cross contraction if elongated, there is a danger of movement. This will distort the impression.

Furthermore, presently used impression trays made of plastic or brass tend to flex easily along its sides or legs. When the tray is inserted into a mouth, the pressure exerted on the legs, by the impression material, can cause the legs of the tray to spread and when force is applied to the outer side of the legs to remove the tray, the legs will flex. This motion in the legs of the tray causes the impression to be disfigured. Applying a force to the handle portion for releasing the tray from the mouth also causes the tray to bend, further distorting the impression.

Most presently used trays also prevent good aligning with a normal bite. These trays do not have a curvature to align with a normal bite radius. The presently used trays also cannot sit flatly on a surface when removed from the mouth, and have other structures which make their use difficult.

It is therefore needed to produce an impression tray which avoids the aforementioned problems and provides improvements and ease in the formation of dental restorations.

SUMMARY OF THE INVENTION

It is, therefore, an object of the present invention to produce an impression tray having a rigid structure which will produce an impression with a minimal possibility of deformation.

It is a further object of the invention to produce an impression tray having openings on all of its sides.

It is another object of this invention to produce an impression tray in which each of the openings along the sides are provided with a shoulder for impression material to lock behind when displaced through the openings.

A still further object of the present invention to produce an impression tray in which all openings on the base are provided with an undercut shoulder.

An even further object of the present invention is to produce an impression tray having a platform structure on the bottom of the base to provide reservoir space, beneath the openings in the base, for impression material to flow when displaced and also for adding rigidity to the tray.

Another object of the present invention is to produce an impression tray in which the platform structure on the base is flat, to lie evenly on a surface on which it is placed.

A further object of the present invention is to produce an impression tray having an arcuate dip in the bite portion to align with the normal shape of teeth within a mouth while not affecting the flat base surface.

A still further object of the present invention is to produce an impression tray having ribs on the top of the base for adding further rigidity to the base.

The impression tray of the present invention has a mouthpiece shaped, generally, to conform with at least a portion of a dental bite radius of a mouth. This impression tray can be used for producing impressions of both the upper and lower teeth in a mouth and also to produce partial impressions such as sectional and quadrant impressions. It has a handle attached to the mouthpiece. The mouthpiece includes an outer wall and an inner wall spaced from each other and connected by a base.

The outer wall serves as a point of attachment for the handle and includes a number of vertical slits which extend through the wall and are spaced along its length. The slits each have a shoulder within, facing outside of the mouthpiece. The shoulders are for engagement with impression material displaced through the slits.

The inner wall has identical vertical slits spaced around its length communicating with the outer slits. The inner wall may also be in the form of a palate extending across the inner diameter of the base for use in producing impressions of the upper bite radius although the inner wall may conform to the shape of the outer wall for both upper, lower and partial bite impressions. The slits are, although, not present at the mid-section of the inner wall which conforms to the shape of the outer wall. The base of the mouthpiece has holes all along its length. Alternating with every two holes are ribs along a top of the base. Along the bottom of the base is a platform structure forming reservoirs. Each reservoir encompasses one hole and forms a shoulder around the bottom side of each respective hole. The platform structure may be produced from rails extending along the length of the base and a number of smaller interconnecting bars extending along the width of each base forming a grill structure. The spacing of the smaller bars will coincide with the ribs along the top of the base. The rails and bars on the bottom and ribs on the top of the base add to the rigidity of the mouthpiece.

The aforementioned objects, features and advantages of the invention will, in part, become obvious from the following more detailed description of the invention, when taken in conjunction with the accompanying drawings, which form an integral part thereof.

DETAILED DESCRIPTION OF THE PREFERRED EMBODIMENT

Figure 1:
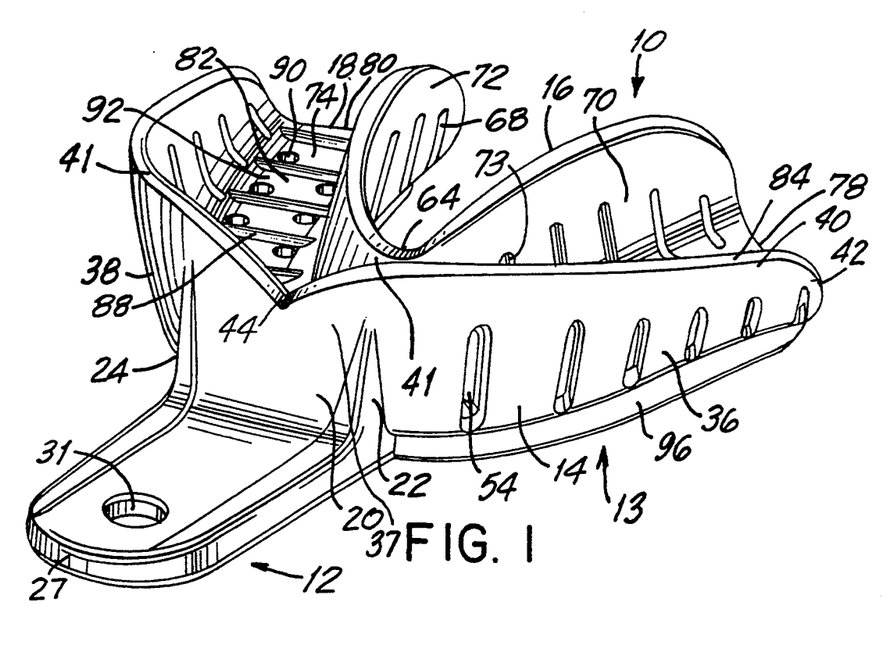
FIG. 1 is a perspective view of the mandibular (lower) impression tray of the present invention.
Figure 2:
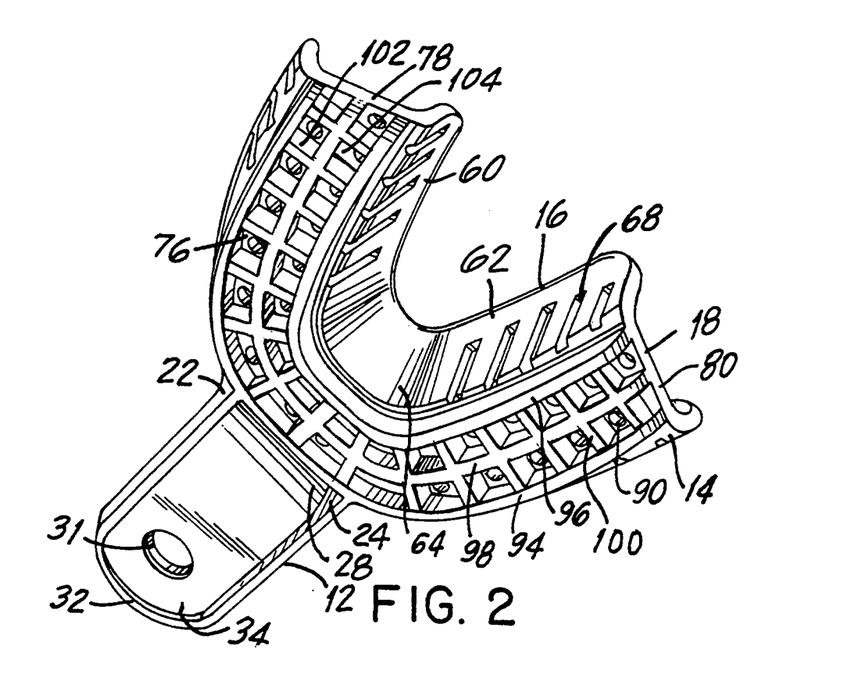
FIG. 2 is a perspective view of the bottom of the impression tray of the present invention.
Figure 6:
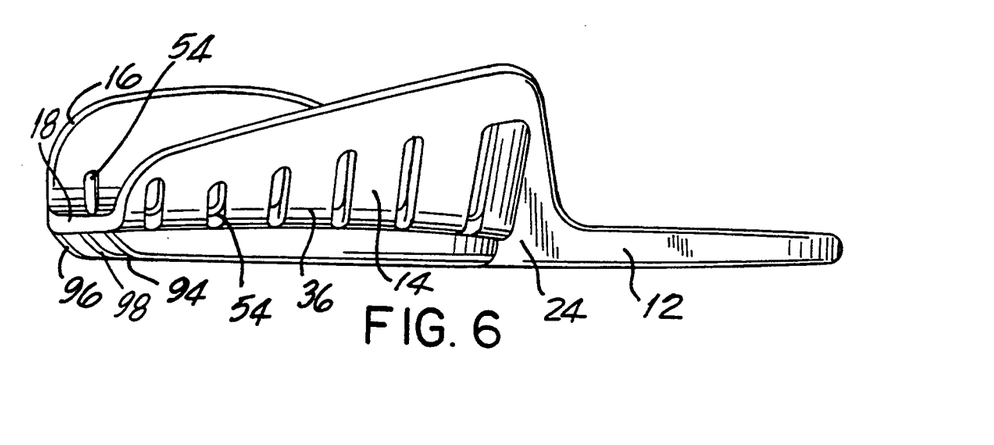
FIG. 6 is a side view of the impression tray of the present invention.

Referring now to FIGS. 1, 2, and 6, a preferred embodiment of the impression tray of the present invention is illustrated.

The impression tray is indicated generally by the number 10. It includes a handle 12 and a mouthpiece 13. The mouthpiece 13 is composed of an outer wall 14, an inner wall 16, and an interconnecting base 18. The handle 12 is flat and of substantially uniform thickness. At a medial end 20, the handle arcs upward and is attached at a top part of the medial end 20 to the outer wall 14. The handle 12 has first and second opposing side walls, 22 and 24 respectively, which form an additional attachment to the outer wall 14. A recess 28 is formed between the arcuate medial end 20 of the handle 12 and the outer wall 14, and is further defined by the first and second side walls 22, 24. Located at the distal end 27 is a hole 31. This hole 31 extends through the handle 12 and can be used for retaining the tray on a wall through a hook. The handle 12 also includes a peripheral ridge 32 extending around a bottom side 34 thereof and merging, at respective ends, into the first and second side walls 22 and 24. This ridge 32 provides a flat surface along the bottom side 34 of the handle 12 and adds to the rigidity of the handle 12.

Figure 8:
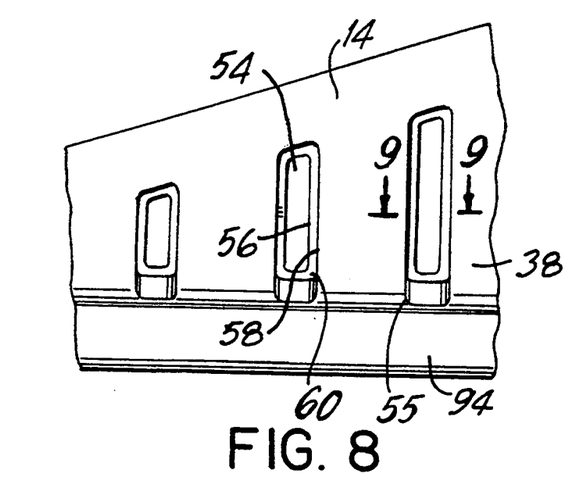
FIG. 8 is a view of the slits in the side of the impression tray of the present invention.
Figure 9:
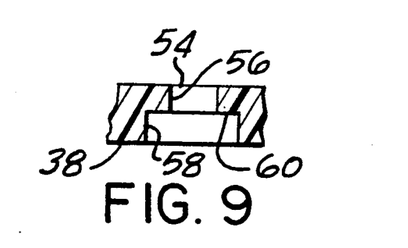
FIG. 9 is a view taken along the line 9—9 of FIG. 8.

The outer wall 14 of the mouthpiece 13 is arcuate in shape, aligning generally to the shape of at least a portion of the outer dental bite radius of the mouth and when used to produce an impression of the entire upper or lower bite radius, resembles the shape of the letter "U", having first and second legs, 36, 38 respectively, and a curved section 37 connecting the first and second legs 36, 38. A top portion 40 of the outer wall 14 extends from a back end 42 along an angled incline, to a peak height 41, and then dips arcuately. When used as a tray for the entire bite radius the top portion extends, along an angled incline, from both the first and second legs 36, 38 of the outer wall 14 to a peak height slightly before the mid-point 44 and then dips arcuately to the midpoint 44. Along the first and second legs 36, 38 and curved section 37 of the outer wall 14 are a number of vertical slits 54. These slits can be seen in FIG. 8 and, more specifically, in FIG. 9. The slits 54 are spaced along the length of the outer wall 14 and each extend a distance from a top portion 40 of the outer wall 14 along the height of the outer wall 14, to a point near the bottom of the outer wall 14. Slits 57 and 59 also exist on the outer wall 14 at a point opening into the recess 28. Each of the slits 54 are narrow on an inner side 56 and wider on an outer side 58 of the outer wall 14. This is due to a shoulder 60 within each slit 54. Each shoulder 60 extends around the entire interior of a respective slit 54 and faces toward the outside of the mouthpiece 13. The shoulder 60 meets both the inner and outer sides 56 and 58 at approximately a 90° angle, thus providing a sharp edge and a side to retain impression material in a locked relationship with the tray 10.

Figure 11:
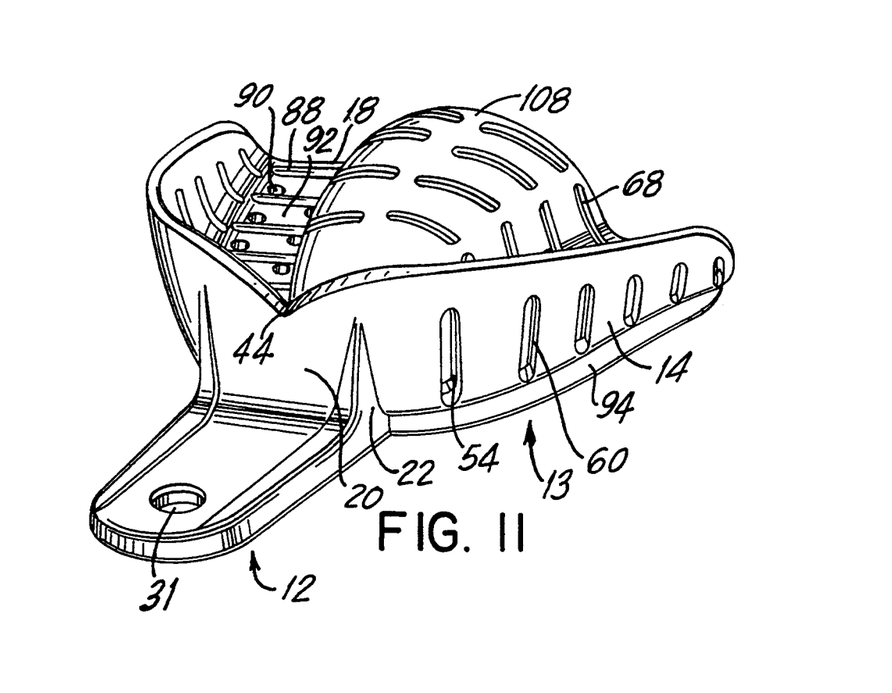
FIG. 11 is a perspective view of the maxillary (upper) impression tray of the present invention having a palate as the inner wall.

The inner wall 16 is also of a shape emulating at least a portion of the inner dental bite radius of a set of teeth. When used to produce an impression of the entire upper or lower dental bite radius, the inner wall may conform with the shape of the outer wall, resembling the shape of the letter "U", having first and second legs and a curved section connecting the first and second legs. The inner wall 16 may also be in the form of a palate 108, as can be seen in FIG. 11, creating an arcuate surface between the legs of the mouthpiece 13 when used solely to produce an impression of the upper dental bite radius. The inner wall 16 is more arcuate than and inclined away from the outer wall 14. The inner wall 16 also extends along and is spaced from the outer wall 14. The outer and inner walls 14, 16 are connected by the interconnecting base 18. The junction with the base is on a bottom end of both the outer and inner walls 14, 16 forming a trough in which the impression material will be placed. The inner wall 16, in other than palate form, is, when manufactured, somewhat arcuate along its top edge and comes to a dip at a curved section 64 thereof. This curved section 64 is rounded for a comfortable fit within a mouth and is at a position lower than the midpoint 44 on the outer wall 14. The inner wall 16, like the outer wall 14, has vertical slits 68 evenly spaced along its width. When in palate form the inner wall 16 has slits 68 spaced all along its surface. The slits 68, although, are not present in the curved section 64 thereof. The slits 68 are identical in structure to the slits 54 of the outer wall 14. The slits 68 are more narrow on the interior side, facing into the trough, or when in palate form facing towards the palate of the mouth, when positioned inside of a patient's mouth, than on the exterior side thereof facing outside the mouthpiece 13 or towards the lower teeth when in palate form. This is due to a shoulder 73 within the slits 68. The shoulder 73 faces in the same direction as the wider side of the slit 68.

When manufactured, both the outer and inner walls 14, 16, respectively, of the impression tray 10 have ends which are rounded, the extent to which the ends are rounded is in conformance with the size of impression tray desired and shape of a mouth corresponding to that size. The trays are produced in different sizes such as small, medium, large, extra large, etc. The dentist can then therefore start with a tray which is suitable for the particular patient. The ends of these walls 14, 16, although they are formed to conform with the dimensions of a normal mouth, relative to the size of the impression tray, may be filed by a dentist so that the ends conform to the mouth of which an impression will be made.

The base 18 extends between the outer and inner walls 14, 16 and is connected to a bottom end of each forming a trough. This can be seen in detail in FIGS. 3 and 7. The base 18 has a top 74, a bottom 76, and first and second distal ends 78, 80. The first and second distal ends 78, 80 are rounded when manufactured. These rounded ends may be filed conforming the tray for use. The impression tray 10 is formed having a length which would extend too deep into most mouths. A dentist will file the ends to conform to the size of the mouth and the depth within the mouth in which the teeth extend if necessary. By filing the ends, the dentist provides for a better, more comfortable fit within the mouth.

The shape of the base 18 conforms to the shape of the teeth within the mouth. The top 74 of the base 18 is formed to conform with the normal shape of teeth. The top 74 is flat along its legs 82, 84 and comes to an arcuate dip at its mid-section 86. This conforms to the shape of teeth in the mouth. The arcuate dip in the top side of the base does not affect the contour of the bottom surface 76 of the base 18. The bottom 76 of the base 18 is flat for stationary placement on a surface.

Figure 3:
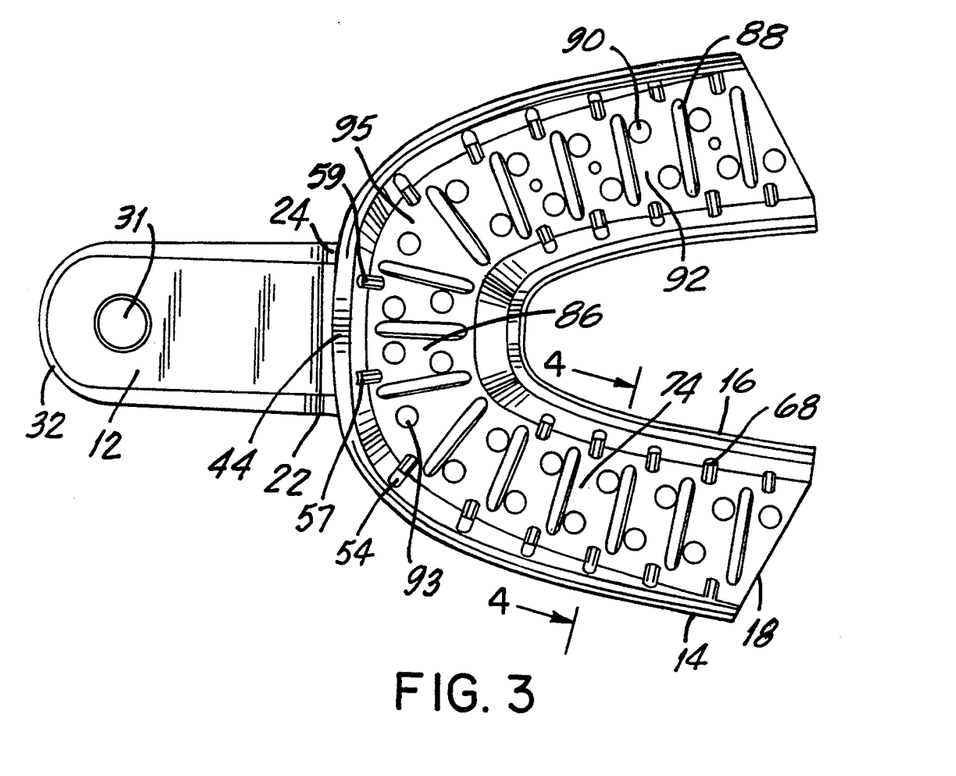
FIG. 3 is a top view of the impression tray of the present invention.

Along the top 74 of the base 18 are spaced ribs 88. These ribs 88 run widthwise, extending between the outer and inner walls 14, 16. The ribs 88 also alternate with the slits 54, 68 on the outer and inner walls 14, 16. One slit 54, 68 for each of the outer and inner walls 14, 16 are disposed between respective pairs of ribs 88. This is true except for the middle area of the mouthpiece 13 in which there are no slits on the inner wall 16. At this point there is only one slit 54 on the outer wall 14 between each pair of ribs 88. Also, on the top 74 of the base 18 are holes 90 which extend through the base 18 to the bottom 76. The holes 90 are spaced along the entire base 18. Between each pair of ribs 88 are two holes 90. A first hole 90 is positioned in one corner of a box 92 formed by each pair of ribs 88. The second hole 90 is positioned in an opposite corner, at a diagonal, to the first hole 90 in the box 92. The only boxes 92 without two holes 90 extending therethrough are the boxes 93 and 95 formed at the rounded corners of the impression plate 10 as shown in FIG. 3. These boxes 93 and 95 each have only one hole 90.

Figure 4:
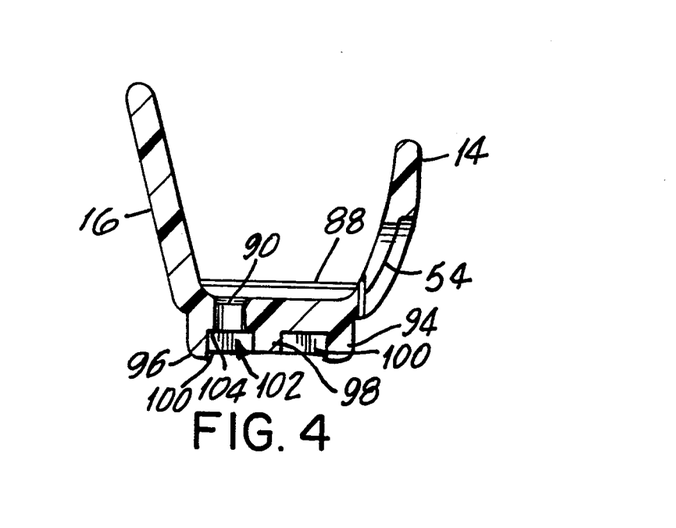
FIG. 4 is a view taken along the line 4—4 of FIG. 3.
Figure 7:
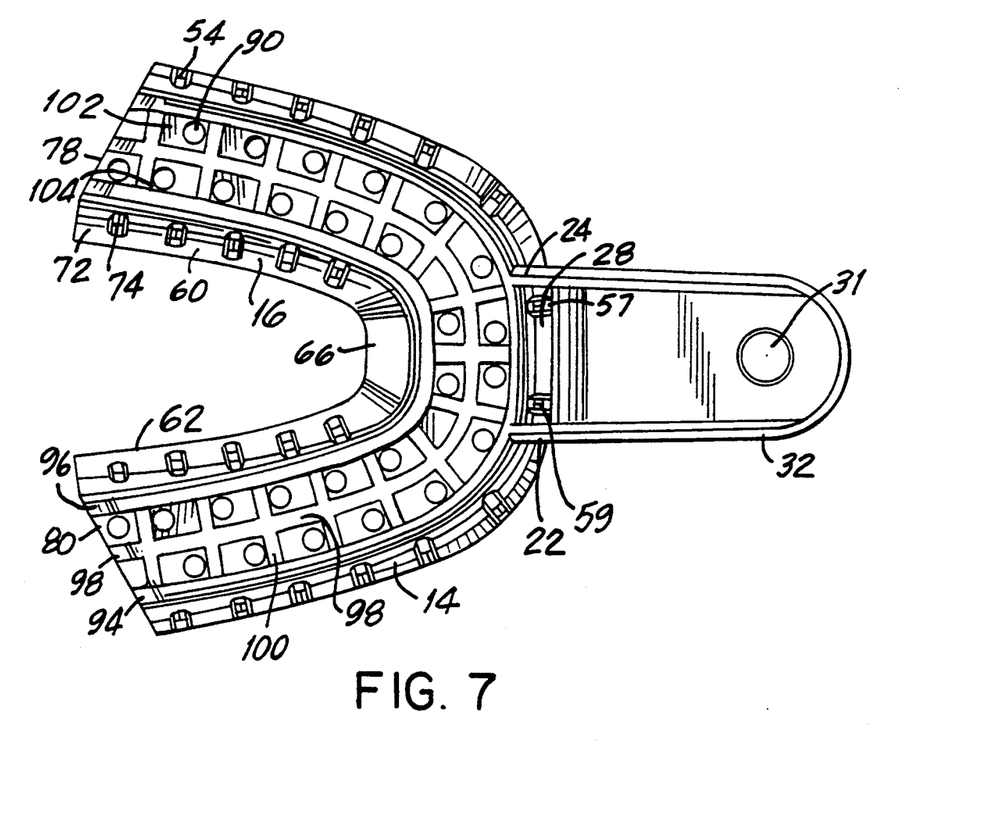
FIG. 7 is a bottom view of the impression tray of the present invention.

Along the bottom 76 of the base 18 is a platform structure. The platform structure may be composed of rails extending along the length of the base and bars which run nearly perpendicular to the rails, as best shown in FIG. 7. There is an outer rail 94 extending along the junction between the outer wall 14 and the bottom 76 of the base 18, an inner rail 96 extending along the junction between the inner wall 16 and the bottom 76 of the base 18. There may also be a middle rail 98 extending along the bottom 76 of the base 18 and positioned between the outer rail 94 and the inner rail 96. The outer and inner rails 94, 96 extend a distance 97 further below the base of the impression tray then the middle rail 98. This provides added room for excess impression material to flow and also greatly reduces slippage of the impression tray sideways when the tray is inserted in the mouth and pressed upon to create a better impression. The fingers of the person making the impression will rest between the inner and outer rails and on top of the middle rail 98 when inserting and removing the tray 10 from the mouth. Also, along the bottom 76 of the base 18, extending between the outer rail 94 and inner rail 96, are spaced dividing bars 100. The dividing bars 100 will extend a distance below the base 18 equal to that of the middle rail 98. These dividing bars 100 are spaced so as to be below a respective rib 88 on the top 74 of the base 18. The combination of the outer, inner and middle rails and the dividing bars 94, 96, 98, 100 respectively, form the platform structure on the bottom 76 of the base 18. The thickness of the rails 94, 96 and 98 and the bars 100 forming the platform structure result in the formation of reservoirs 102 along the bottom 76 of the base 18. Each of these reservoirs 102 are associated with a respective hole 90. The reservoirs 102 further define shoulders 104 formed in the bottom 76 of the base 18 and surrounding the holes 90 in the base 18. A view of a hole 90 extending through the base 18 and into a reservoir 102 can be seen in FIG. 4. The hole 90 extends from the top 74 through the base 18 and into the reservoir 102 formed by the rails 94, 96 and 98 and dividing bars 100. The rails 94, 96 extend downward an equal distance to produce a flat bottom surface. The outer rail 96 also meets, on an even plane, the base of the first and second side walls 22, 24 of the handle 12. This allows the impression tray 10 to sit flatly on a surface.

The impression tray 10 of the present invention is very rigid, allowing for only insignificant bending of the legs or sides. This rigidity comes from the structure of the tray 10. The ribs 88 on the top 74 of the base 18 along with the rails 94, 96 and 98 and bars 100 on the bottom 76 of the base 18, also add rigidity to the base 18 in order to avoid bending of the legs 82, 84, up, down or from side to side. Further rigidity is added by the peripheral ridge 32 around the handle 12. This ridge 32 allows for the impression tray 10 to be removed without bending. If the handle 12 bends when the tray 10 is removed, it will interfere with efforts to remove the tray 10 and may distort the impression.

Figure 10:
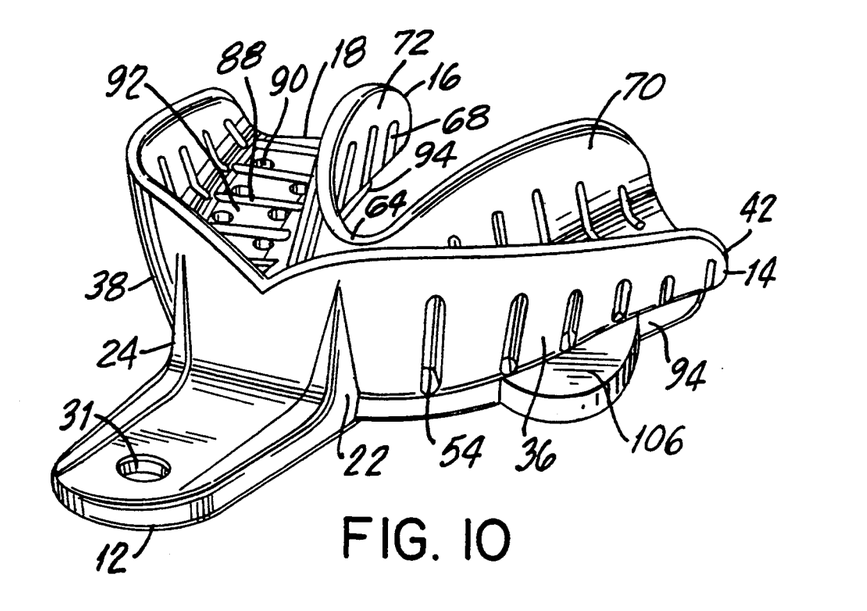
FIG. 10 is a perspective view of the impression tray of the present invention including ledges along the sides.

FIG. 10 illustrates the impression tray 10 of the present invention including ledges 106 positioned at the base of each leg. The ledges 106 are for grasping of the tray while in a mouth after the impression material is fully cured. They aid in the removal of the tray 10 from the mouth.

FIG. 11 shows the impression tray of the present invention designed solely for making impressions of the entire upper bite radius. This embodiment includes a palate 108 as the inner wall. The palate 108 spans the gad between the legs of the tray 10 and includes slits extending all along its surface. These slits are identical to those on the outer wall 14. They include a narrow opening on the side of the palate 108 facing the palate of a mouth when positioned inside a mouth and a wider opening on the opposing side with a shoulder in between.

Figure 12:
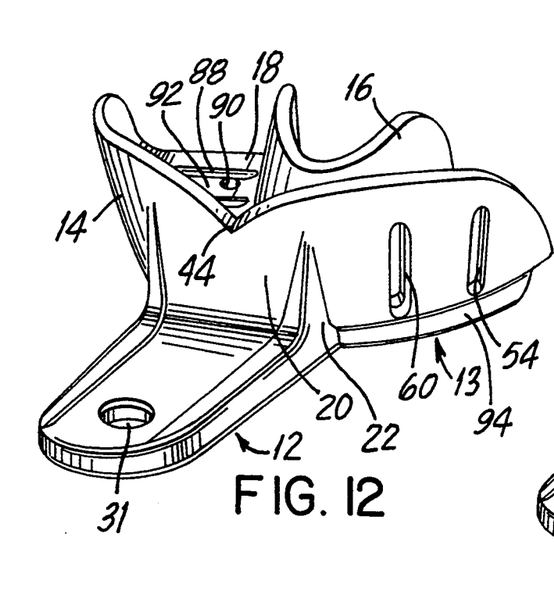
FIG. 12 is a perspective view of the impression tray of the present invention used for making sectional impressions.
Figure 13:
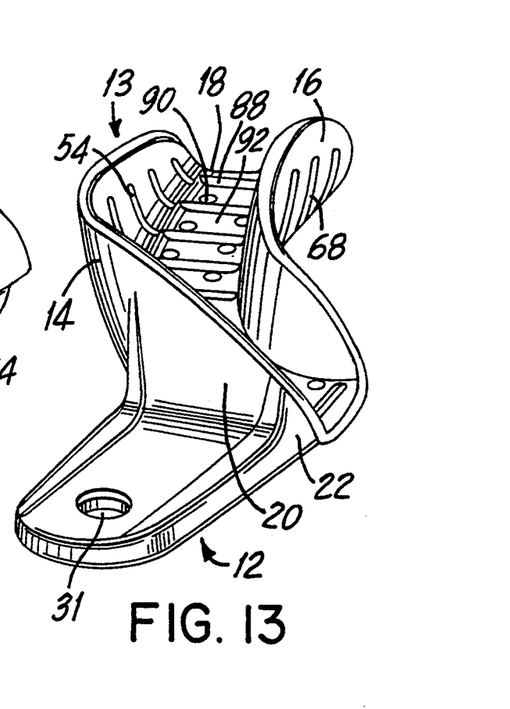
FIG. 13 is a perspective view of the impression tray of the present invention for making quadrant impressions.

FIG. 12 illustrates the impression tray of the present invention having short legs. The short legs adapt this embodiment for forming sectional impressions of the front upper and lower teeth and FIG. 13 illustrates an embodiment adapted for producing quadrant impressions. This embodiment is formed from one leg of the tray for producing an impression of an entire upper or lower bite radius. Although the figure illustrates a tray which may be used for only upper right or lower left bite radius impressions, upper left and lower right bite radius impressions may be made using a tray being the mirror image of the one illustrated, the opposing leg of the tray for making an impression of an entire upper or lower bite radius.

In operation, the impression tray 10 is filled with an impression molding material. Examples of such an impression material are silicone, polyether, irreversible hydrocolloid (alginate) and polysulfide. Any excess material will flow into the slits and holes. The impression tray 10, filled with the impression material, is then placed inside the mouth of the person of whom an impression is desired. It is placed in the mouth in such a manner that the teeth will be within the trough of the mouthpiece 13 of the impression tray 10 formed between the outer wall 14, inner wall 16 and base 18, and surrounded by the impression material when the tray 10 is in position. The dip at the mid-point 44 of the outer wall 14 is positioned for comfortable placement of the impression tray 10 to provide space for the labial frenulum. When making quadrant impressions the side of the labial frenulum on which the tray is placed is dependent upon the type of impression desired, upper left, upper right, lower left or lower right. The handle 12 extends outside the mouth. Pressure is then applied, at the base 18 of the impression tray 10, towards the teeth. The pressure is applied by the dentist pressing on the bottom 76 of the base 18. The dentist will position his fingers into the finger guide formed between the outer and inner rails 94, 96 to avoid slippage of the impression tray due to fingers sliding along the bottom of the tray. The pressure applied causes the impression material to be displaced by the teeth. Thus, the impression material is forced through the slits 54, 68 along the outer and inner walls 14, 16, and holes 90, in the base 18 of the impression tray 10.

When the impression material is pushed through the slits 54, 68, it seeps behind the shoulders 58, 69 within the slits 54, 68 respectively. By seeping behind the shoulders 58, 69, the impression material becomes, upon curing, locked behind the shoulders 58, 69 and attached to the impression tray 10. The same effect occurs when the impression material is pushed through the holes 90 in the base 18. The impression material seeps into the reservoirs 102 and behind the shoulders 104 and, upon curing, locks, behind the shoulders 104, to the impression tray 10.

Furthermore, the reservoirs are of such size that a large amount of the excess impression material used can fit within the reservoirs 102 and not extend outward past the rails 94, 96 and 98 and the bars 100 on the base 18. Any excess material which overflows the rails are cut by knife after the tray is removed from the patient's mouth.

Once the impression tray 10 has been within the mouth long enough for the material to fully cure, the tray may be removed. The ledges 106 are supplied on either side of the outer wall 14 as an aid in removing the tray. When it is desired to remove the tray the ledges are used to exert pressure to release the tray and impression material from the teeth an then remove the tray from the mouth.

There has been disclosed, heretofore, the best embodiment of the invention presently contemplated. However, it is to be understood that various changes and modifications may be made thereto without departing from the spirit and scope of the invention.

We claim;

1. A dental impression tray, comprising:
   a mouthpiece having:
   outer and inner walls;
   a rigid base connected between and at a bottom side of both the outer wall and the inner wall together therewith forming a trough shaped to conform with at least a portion of a dental bite radius; and
   a handle connected to an outer side of the outer wall, a plurality of holes extending through the base, and a rigid platform structure along the underside of the base and extending between said outer and inner walls and forming a reservoir surrounding each hole in the base for collection of displaced impression material.

2. An impression tray as claimed in claim 1, wherein the platform structure on the bottom of the base comprises:
   a first rail attached to and extending along the length of the base at the connection between the base and the outer wall;
   a second rail attached to and extending along the length of the base at the connection between the base and the inner wall; and
   wherein the combination of the first and second rails defines the reservoir surrounding the holes in the base.

3. An impression tray as claimed in claim 2, wherein the platform structure further comprises a third rail attached to and extending along the length of the base at a position between the first and second rails and a plurality of bars positioned substantially perpendicular to the first, second and third rails and spaced along the length of the base.

4. An impression tray as claimed in claim 3, wherein the first and second rails extend a greater distance below the base than both the third rail and the plurality of bars creating a finger guide for reducing the possibility of sliding of the impression tray when force is applied to the base.

5. An impression tray as claimed in claim 4, wherein the handle includes a peripheral ridge extending around a bottom edge thereof, the ridge connecting at each end, on an even plane, to the first rail forming a flat surface.

6. An impression tray as claimed in claim 2, further comprising a plurality of ribs spaced along the base, within the trough, extending between the inner and outer walls, wherein between each pair of adjacent ribs are two slits, one on the inner wall and one on the outer wall.

7. An impression tray as claimed in claim 6, wherein a curved section of the inner wall does not have vertical slits and, one vertical slit on the outer wall exists between each pair of adjacent ribs in a curved section of the mouthpiece.

8. An impression tray as claimed in claim 6, wherein the plurality of ribs are spaced so that two holes are between each pair of adjacent ribs.

9. An impression tray as claimed in claim 8, wherein one hole is present between each pair of adjacent ribs at corner points of the base.

10. An impression tray as claimed in claim 8, wherein the spacing of the plurality of ribs on the top of the base coincides with the spacing of the plurality of bars on the bottom of the base.

11. A dental impression tray as claimed in claim 1, wherein the outer wall and inner wall each have a plurality of vertical slits, spaced along the length thereof; including a shoulder within each vertical slit so that a first opening of each vertical slit is more narrow than a second opening of each vertical slit, the first opening facing the trough and the second opening facing outside the mouthpiece, and wherein impression material, when displaced through the vertical slits seeps behind the shoulders, forming an interlocking relationship, upon curing, with the shoulder.

12. An impression tray as claimed in claim 1, wherein a first end of the handle is arcuate and connects to the outer wall at a top edge thereof.

13. An impression tray as claimed in claim 12, wherein the handle further includes first and second side walls connected between the handle and the outer wall.

14. An impression tray of claim 13, wherein a recess exists between the handle, the first and second side walls and the outer wall.

15. An impression tray of claim 14, wherein vertical slits exists in the outer wall at the position of the recess.

16. The impression tray as claimed in claim 1, wherein the inner wall is in the form of a palate.

17. An impression tray as claimed in claim 1, wherein the rigid platform structure forms a plurality of individual reservoirs, each individual reservoir surrounding a corresponding one of said plurality of holes.

18. A dental impression tray, comprising
a mouthpiece, having:
outer and inner walls; and
a base connected between and at a bottom side of both the outer wall and the inner wall together therewith forming a trough shaped to conform with at least a portion of a dental bite radius; and
a handle connected to an outer side of the outer wall at a middle position thereof, wherein the outer wall and inner wall each have a plurality of vertical slits, spaced along the length thereof, including a shoulder within each vertical slit, each shoulder having a flat face extending perpendicular to its respective vertical slit, so that a first opening of each vertical slit is more narrow than a second opening of each vertical slit, the first opening facing the trough and the second opening facing outside the mouthpiece, and wherein impression material, when displaced through the vertical slits seeps behind the flat face of each shoulder, forming an interlocking relationship, upon curing, with the shoulder.

19. An impression tray as claimed in claim 18, further comprising:
a plurality of holes extending through the base of the impression tray; and
a plurality of ribs spaced along the top of the base extending between the inner and outer walls, wherein between each pair of adjacent ribs are two slits, one on the inner wall and one on the outer wall, and two holes extending through the base.

20. An impression tray as claimed in claim 19, wherein a curved section of the inner wall does not have vertical slits and one vertical slit on the outer wall exists between each pair of adjacent ribs in a curved section of the mouthpiece.

21. An impression tray as claimed in claim 19, wherein one hole is present between each pair of adjacent ribs at corner points of the base.

22. An impression ray as claimed in claim 19, further comprising a platform structure formed to a bottom of the base having:
a first rail attached to and extending along the length of the base at the connection between the base and the outer wall;
a second rail attached to and extending along the length of the base at the connection between the base and the inner wall;
a third rail attached to and extending along the length of the base at a position between the first and second rails; and
a plurality of bars positioned substantially perpendicular to the first, second and third rails and spaced along the length of the base, wherein the platform structure forms a reservoir surrounding each hole in the base for collection of displaced impression material and also provides a flat surface for level placement of the impression tray on a surface.

23. An impression tray as claimed in claim 22, wherein the handle includes a peripheral ridge extending around a bottom edge thereof, the ridge connecting at each end, on an even plane, to the first rail forming a flat surface.

24. An impression tray as claimed in claim 22, wherein the spacing of the plurality of ribs on the to of the base coincides with the spacing of the plurality of bars on the bottom of the base.

25. An impression tray as claimed in claim 18, wherein a first end of the handle is arcuate and connects to the outer wall at a top edge thereof.

26. An impression tray as claimed in claim 25, wherein the handle further includes first and second side walls connected between the handle and the outer wall.

27. An impression tray of claim 26, further comprising a recess between the handle, the first and second side walls and the outer wall.

28. An impression tray of claim 27, wherein vertical slits exist in the outer wall at the position of the recess formed between the handle, first and second side walls and the outer wall.

* * * * *